United States Patent
Dertinger et al.

(10) Patent No.: US 6,383,735 B1
(45) Date of Patent: May 7, 2002

(54) FIBROMYOMA OR CARCINOMA CORPORIS UTERI

(75) Inventors: Hermann Dertinger, Heidelberg; Gudrun Knedlitscheck, Karlsruhe; Ilya Krouglikov, Eggenstein-Leopoldshafen; Evguenia Skobeltzin; Karl-Friedrich Weibezahn, both of Karlsruhe, all of (DE)

(73) Assignee: Forschungszentrum Karlsruhe GmbH, Karlsruhe (DE)

(*) Notice: Subject to any disclaimer, the term of this patent is extended or adjusted under 35 U.S.C. 154(b) by 0 days.

(21) Appl. No.: 09/245,267

(22) Filed: Feb. 5, 1999

Related U.S. Application Data

(63) Continuation-in-part of application No. PCT/EP97/03016, filed on Jun. 10, 1997.

(30) Foreign Application Priority Data

Aug. 7, 1996 (DE) .......................... 196 31 850

(51) Int. Cl.$^7$ ............................ G01N 33/48; C12Q 1/00; C12Q 1/02
(52) U.S. Cl. ............................... 435/4; 435/29; 436/63; 436/64
(58) Field of Search ..................... 435/29, 2, 4, 243, 435/7.21; 436/63, 64, 169, 177, 178

(56) References Cited

U.S. PATENT DOCUMENTS

| | | | |
|---|---|---|---|
| 3,916,176 A | 10/1975 | Alien et al. ............... 235/151.3 |
| 5,403,719 A | 4/1995 | Adachi et al. ............... 435/29 |
| 5,572,028 A | 11/1996 | Moscovitch et al. ........ 250/337 |
| 6,124,087 A | * 9/2000 | Skobellzin et al. ............ 435/2 |

FOREIGN PATENT DOCUMENTS

| | | |
|---|---|---|
| WO | WO 90/02337 | 3/1990 |
| WO | WO 93/03348 | 2/1993 |
| WO | WO 94/03825 | 2/1994 |

OTHER PUBLICATIONS

J. Boone, "X–Ray Spectral Reconstruction From Attenuation Data Using Nerual Networks", Med. Phys. (4) Jul./Aug. 1990.

* cited by examiner

*Primary Examiner*—Ardin H. Marschel
(74) *Attorney, Agent, or Firm*—Klaus J. Bach

(57) ABSTRACT

In a process for rapidly and inexpensively diagnosing malignant diseases or their precursor stages, samples of arterial and/or capillary blood and of venous blood are withdrawn from a patient and the percentage shares of three groups of blood cells in the blood samples are determined wherein a first group includes blood cells of a size $\leq 8$ $\mu$m, a second group includes blood cells of a 9 $\mu$m and 10 $\mu$m and the third group includes blood cells of a size $\geq 11$ $\mu$m. The percentage shares are multiplied by weighting factors $\alpha_1$ and $\beta_1$, and the values $$y = \Sigma \alpha_i [(N_i)^A] - \Sigma \alpha_i [(N_i)^V]$$

and $$x = \Sigma \beta_i [(N_i)^A] - \Sigma \beta_i [(N_i)^V],$$

are calculated and from the locations of x and y in an x/y coordinate system, the presence of Ca. corp. uteri or its precursor stages is determined.

3 Claims, 1 Drawing Sheet

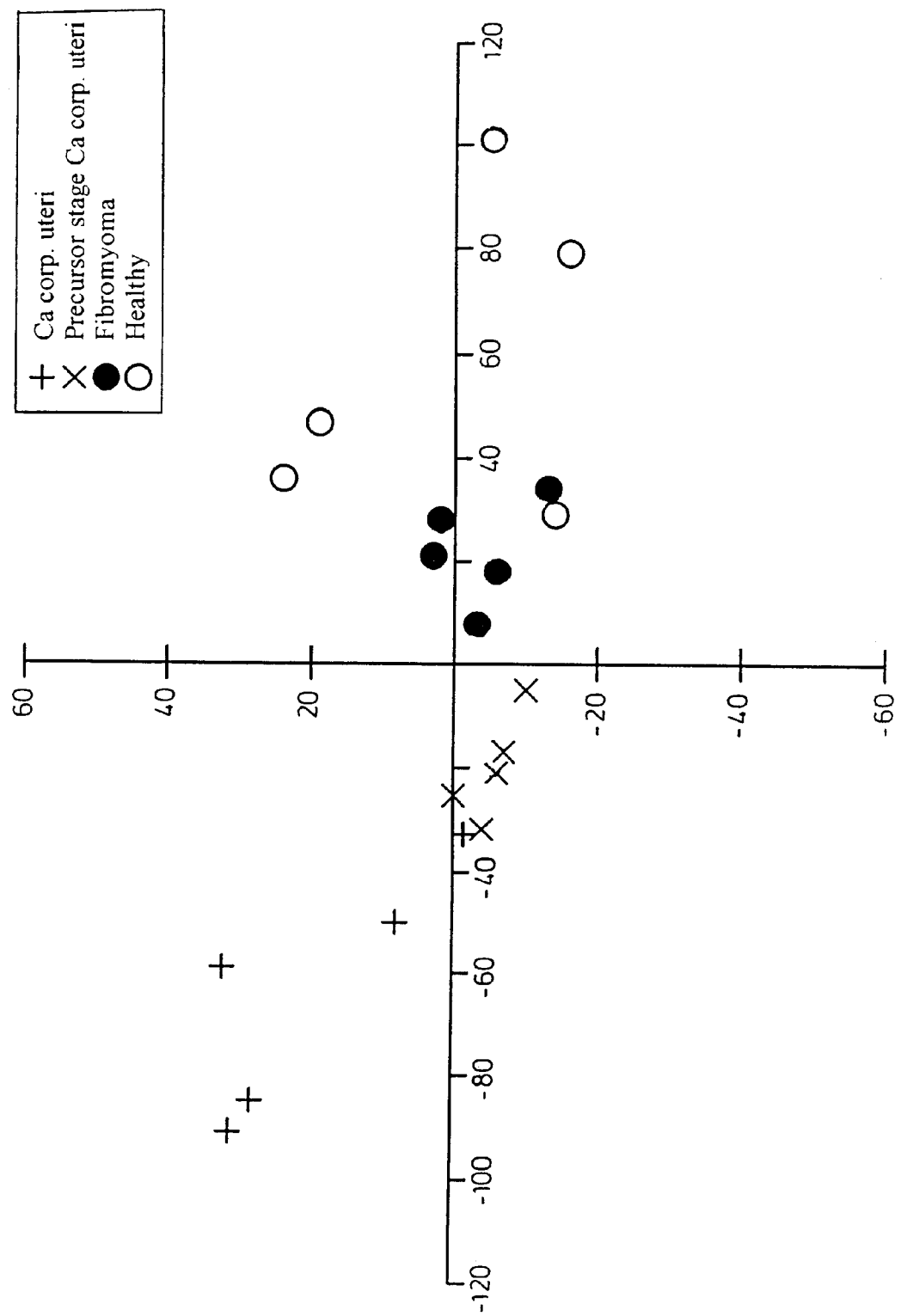

FIBROMYOMA OR CARCINOMA CORPORIS UTERI

This is a Continuation-in-Part application of international application PCT/EP97/03016 filed of Jun. 10, 1997 and claiming the priority of German application 196 31 850.5 filed Aug. 7, 1996.

BACKGROUND OF THE INVENTION

The invention relates to a process for rapidly diagnosing a malignant disease or the precursor stages thereof from blood samples including arterial and venous blood.

For the diagnosis of malignant diseases imaging procedures such as X-ray, ultrasound, computer tomography, core spin tomography and also histological examinations of biopsis material, antibody tests and tests for more or less specific tumor markers are utilized. The last mentioned tests are performed with histological preparations and also with blood serum. The tumor markers are generally very specifically indicative only for certain types of tumors.

Problems generally occur in that these procedures have only an unsatisfying accuracy and cannot distinguish sufficiently clearly between malignant and benign types and precursor stages. For a safe diagnosis, several of these procedures are generally needed. Some of the imaging procedures involve substantial radiation exposure; and the biopsy represents a surgical procedure, which may even result in a spreading of tumor cells. In addition, these procedures are all relatively expensive. In some cases, reliable results are available only after several days of continuous evaluation.

Printed publication (1) discloses a process for the diagnosis of malignant diseases wherein arterial and venous blood of a patient is examined. In this process, the various cell populations and/or sub-populations are determined and the results of these determinations for venous and arterial blood are compared.

It is the object of the present invention to provide a rapid and economic process for diagnosing malignant diseases and their precursor stages which does not rely on imaging procedures and which can be performed in a laboratory in a simple, fast and inexpensive way.

SUMMARY OF THE INVENTION

In a process for rapidly and inexpensively diagnosing malignant diseases or their precursor stages, samples of arterial and/or capillary blood and of venous blood are withdrawn from a patient and the percentage shares of three groups of blood cells in the blood samples are determined wherein a first group includes blood cells of a size $\leq 8$ $\mu$m, a second group includes blood cells of a 9 $\mu$m and 10 $\mu$m and the third group includes blood cells of a size $\geq 11$ $\mu$m. The percentage shares are multiplied by weighting factors $\alpha_1$ and $\beta_1$, and the values $$y = \Sigma\alpha_i[(N_i)^A] - \Sigma\alpha_i[(N_i)^V]$$

and $$x = \Sigma\beta_i[(N_i)^A] - \Sigma\beta_i[(N_i)^V],$$

are calculated and from the locations of x and y in an x/y coordinate system, the presence of Ca. corp. uteri or its precursor stages is determined.

With the process according to the invention peripheral blood cells, preferably the lymphocyte population is examined. These cells are removed from the organism with arterial and/or capillary blood. The arterial blood can be taken from a peripheral artery. Instead of arterial blood, capillary blood can be used which can be taken from a fingertip or an earlobe of a patient.

In addition, venous blood is taken for example from an arm vein of a patient. The arterial blood and/or the capillary blood as well as the venous blood are examined outside the body. For the blood examination a standard blood smear test is suitable. In the test, size ratios of groups of the cells, particularly lymphocytes, are determined and are subjected to a mathematical analysis.

For performing the process, blood smears may be prepared on a microscope slide from the blood taken from an artery and/or a capillary such as the fingertip and from the blood taken from a vein. The blood cells can be dried, fixed and stained by standard procedures.

Thereafter, a size histogram of arterial and/or capillary (index A) and venous (index V) blood cells, preferably of the lymphocyte population is prepared. This can be done by microscopic measurement of diameters of about 200 blood cells, particularly about 200 lymphocytes from the smear. To this end, the respective percentage content $(N_i)^A$ or, respectively, $(N_i)^V$ in the three size ranges $(1) \leq 8$ $\mu$m, preferably 6 $\mu$m to 8 $\mu$m, (2) 9 $\mu$m and 10 $\mu$m and $(3) \geq 11$ $\mu$m, preferably 11 $\mu$m to 16 $\mu$m are determined with an accuracy of 1 $\mu$m (that is the blood cell diameter values are rounded to the nearest $\mu$m number). This is done in such a way that, for each of the three cell size groups in the total range of from about 6 $\mu$m to 16 $\mu$m in the arterial ($^A$) as well as in the venous blood ($^V$) the percentage content $(N_i)^A$, or respectively, $(N_i)^V$ of each of the three size ranges of the total number of the respective blood cell type is determined.

Lymphocytes <6 $\mu$m and >16 $\mu$m are generally present only in small numbers. Besides the measurement of smear samples any other procedure is suitable whereby the percentage shares of the three groups corresponding to the size ranges mentioned on the basis of the respective blood cell type can be determined.

The percentage shares of blood cells of the respective group are multiplied by weighting factors. In a first step, initially the percentage shares of the arterial and/or the capillary blood as well as the percentage shares of the venous blood are multiplied by a first weighting factor $\alpha_i$ which preferably for the first group of $\leq 8\mu$m has the value 4, for the second group of 9 $\mu$m and 10 $\mu$m has the value 2, and for the third group of $\geq 11$ $\mu$m has the value 4.

In any case, the weighting factors $\alpha_i$ for the first and the third groups should be essentially the same whereas the weighting factor for the second group is smaller.

In this way, the values of $\alpha_i[(N_i)^A]$ (arterial blood and (or capillary blood) and $\alpha_i[(N_i)^V]$ (venous blood) are obtained for the first, the second and the third group.

The values of $\alpha_i[(N_i)^A]$ and $\alpha_i[(N_i)^V]$ of the first, second and third group are added up whereby $\Sigma\alpha_i[(N_i)^A]$ and $\Sigma\alpha_i[(N_i)^V]$ are obtained.

In an analog manner, subsequently the percentage shares of the arterial and/or capillary blood $[(N_i)^A]$ and also the percentage shares of the venous blood $[(N_i)^V]$ are multiplied by a second weighting factor $\beta_i$, which preferably for the first group of $\leq 8$ $\mu$m has the value 8, for the second group of 9 $\mu$m and 10 $\mu$m has the value 4, and for the third group of $\geq 11$ has the value 2. With the selection of other weighting factors $\beta_i$, it has to be taken into consideration that the numerical value of the weighting factors $\beta_i$ of the first group is the highest and is the smallest for the third group. In this way, the value of $\beta_i[(N_i)^A]$ and $\Sigma\beta_i[(N_i)^V]$ are obtained for the first, second and third group.

The values of $\beta_i[(N_i)^A]$ and $\beta_i[(N_i)^V]$ of the first, the second and the third group are added up whereby $\Sigma\beta_i[N_i)^A]$ and $\Sigma\beta_i[(N_i)^V]$ are obtained.

Subsequently, the differences $$X=\Sigma\beta_i[(N_i)^A]-\Sigma\beta_i[(N_i)^V].$$

$$X=\Sigma\beta_i[(N_i)^A]-\beta_i[(N_i)^V]$$

are calculated. The values for x and y represent for a particular patient characteristic values which can be plotted graphically in an x/y coordinate system as a point. From the position of the point, it can be concluded whether the patient is healthy, is in a precursory cancer stage, particularly a fibromyoma, or has uterus cancer (Ca. corp uteri).

The invention will be described below in greater detail on the basis of the accompanying drawing.

BRIEF DESCRIPTION OF THE DRAWINGS

FIG. 1 shows a coordinate system with a base x and an ordinate y showing the characteristic x and y values of a number of female patients examined.

For the evaluation of blood smears, the percentage shares $(N_i)^A$ for arterial and/or capillary blood and for venous blood and also the percentage shares $(N_i)^V$ for each of the lymphocyte groups (1) 6 $\mu$m to 8 $\mu$m, (2) 9 $\mu$m and 10 $\mu$m and (3) 11 $\mu$m to 16 $\mu$m are calculated. This is done by first counting the number of lymphocytes in the first group including the lymphocytes of the sizes 6 to 8 $\mu$m in the arterial and/or capillary blood and representing the number of these lymphocytes as percentage shares of the total number of lymphocytes. In this way, $(N_1)^A$ for the first group is obtained. The counting and calculating of the share is repeated for the second $(N_2)^A$ and the third $(N_3)^A$ group which include the lymphocytes of the sizes 9 $\mu$m and 10 $\mu$m and of the sizes 11 $\mu$m to 16 $\mu$m.

Subsequently, the lymphocytes in the venous blood are counted in the same way for each group and their percentage share $[(N_i)^V]$ is determined. Then the values of $[(N_i)^A]$ and $[(N_i)^V]$ are multiplied, one after the other, with by the weighting factors $\alpha_i$ and $\beta_i$.

The procedure is shown below for a healthy female patient with the following percentage values:

a) multiplication by the weighting factor $\alpha_i$:

|  | $[(N_i)^A]$ in [%] | $[(N_i)^V]$ in [%] | $A_s$ |
|---|---|---|---|
| First group | 48 | 32 | 4 |
| Second group | 31 | 28.5 | 2 |
| Third group | 21 | 39.5 | 4 |
|  | $\Sigma\alpha_i[(N_i)^A] = 338$ | $\Sigma\alpha_i[(N_i)^V] = 343$ |  | b) multiplication by the weighting factor $\beta_i$:

|  | $[(N_i)^A]$ in [%] | $[(N_i)^V]$ in [%] | $\beta_i$ |
|---|---|---|---|
| First group | 48 | 32 | 8 |
| Second group | 31 | 28.5 | 4 |
| Third group | 21 | 39.5 | 2 |
|  | $\Sigma\beta_i[(N_i)^A] = 550$ | $\Sigma\beta_i[(N_i)^V] = 449$ |  |

Then the differences $$Y=\Sigma\alpha_i[(N_i)^A]-\Sigma\alpha_i[(N_i)^V]=338-343=-5$$

$$X=\Sigma\alpha_i[(N_i)^A]-\Sigma\beta_i[(N_i)^V]=550-449=+101$$

are calculated. In a x/y coordinate system, the values represent a point, which is disposed near the right branch of the base.

This particular point is shown in the coordinate system of FIG. 1 together with other points, which were determined for patients suffering from a fibromyoma and from Ca. corp. uteri.

The evaluation of the characteristic values of several patients in the coordinate system shows that for, healthy patients, the value for x is positive and greater than 20. Patients with a fibromyoma also show a positive value for x, which however is smaller and is in the range of 0 to 20. For patients suffering from Ca. corp. uteri, the x values were always negative.

What is claimed is:

1. A process for rapidly diagnosing Fibromyoma or carcinoma corporis uteri or their precursor stages, comprising the steps of:

a) providing two blood samples of a patient of which one includes at least one of arterial and capillary blood (index A) and the other includes venous blood (index V), bi) determining for each sample the percentage share $N_i$ of blood cells of a first group i=1, which includes blood cells of a size of 8 $\mu$m and smaller than 8 $\mu$m, bii) determining for each sample the percentage share $N_i$ of blood cells of a second group i=2, which includes blood cells of a size of 9 $\mu$m and 10 $\mu$m, biii) determining for each sample the percentage share $N_i$ of blood cells of a third group i=3, which includes blood cells of a size of 11 $\mu$m and greater than 11 $\mu$m, all on the basis of the total number of blood cells and for arterial and capillary blood $[(N_i)^A]$ as well as for venous blood $[(N_i)^V]$, c) multiplying the values obtained for $[(N_i)^A]$ and $[(N_i)^V]$ each with a weighting factor $\alpha_i=4$, for the first and the third groups, and the weighting factor $\alpha_i=2$ for the second group such that the values $\alpha_i[(N_i)^A]$ and $\alpha_i[(N_i)^V]$ are obtained, d) multiplying the values obtained for $[(N_i)^A]$ and $[(N_i)^V]$ each with a weighting factor $\beta_i=8$ for the first group, a weighting factor $\beta_i=4$ for the second group and a weighting factor $\beta_i=2$ for the third group, whereby the values $\beta_i[(N_i)^A]$ and $\beta_i[(N_i)^V]$ are obtained, e) calculating the differences $$y=\Sigma\alpha_i[(N_i)^A]-\Sigma\alpha_i[(N_i)^V]$$

and $$x=\Sigma\beta_i[(N_i)^A]-\Sigma\beta_i[(N_i)^V],$$

and f) determining the deviation of the values x and y obtained from the blood samples of the patient from a comparative collection of the x and y values obtained from blood samples of healthy persons, and g) determining from the deviation of the values x and y from the respective values found in blood samples of healthy persons whether the patient is afflicted by fibromyoma or carcinoma corporis uteri or a precursor stage thereof.

2. A process according to claim 1, wherein said blood cells represent lymphocytes and the number of lymphocytes is employed as the total number of blood cells.

3. A process according to claim 1, wherein the first group includes blood cells of 6 $\mu$m to 8 $\mu$m and the third group includes blood cells of 11 $\mu$m to 16 $\mu$m.

* * * * *